United States Patent [19]

Cocuzza et al.

[11] 4,033,617
[45] July 5, 1977

[54] PROCESS FOR THE PURIFICATION OF ETHYLENE OXIDE

[75] Inventors: Gioacchino Cocuzza, Catania; Gianni Torreggiani, Busto Arsizio (Varese); Michele Sfregola, Bergamo, all of Italy

[73] Assignee: Societa' Italiana Resine S.I.R. S.p.A., Milan, Italy

[22] Filed: July 8, 1976

[21] Appl. No.: 703,342

[30] Foreign Application Priority Data

July 8, 1975 Italy .............................. 25177/75

[52] U.S. Cl. .............................. 203/27; 203/36; 203/38; 203/74; 203/75; 202/198; 62/31; 55/50; 55/56; 55/68; 260/348 R; 260/348.5 R; 203/29

[51] Int. Cl.² .................. B01D 3/14; C07D 303/04

[58] Field of Search ............... 203/27, 14, 29-38, 203/87, 73-80, 81-84; 202/198; 260/348 R; 62/24, 31; 55/50, 56, 68

[56] References Cited

UNITED STATES PATENTS

| 3,165,539 | 1/1965 | Lutz | 260/348 R |
| 3,174,262 | 3/1965 | Lutz | 55/50 |
| 3,418,338 | 12/1968 | Gilman et al. | 260/348 R |
| 3,745,092 | 7/1973 | Van der Water | 260/348.5 R |

Primary Examiner—Wilbur L. Bascomb, Jr.
Attorney, Agent, or Firm—Sughrue, Rothwell, Mion, Zinn & Macpeak

[57] ABSTRACT

Crude ethylene oxide present in the dilute aqueous solution resulting from the extraction with an aqueous solvent of ethylene oxide from the gaseous stream obtained by catalytic oxidation of ethylene is purified by desorption, liquefaction, distillation in a fractionating column and final desorption treatment to remove absorbed non-condensable gases. The fractionating column is heated by condensation of the water vapor evolved during desorption and a liquid stream of ethylene oxide rich in acetaldehyde is discharged from the bottom, treated to convert a fraction of said acetaldehyde into high-boiling products, distilled to remove the latter as bottoms and returned to the fractionating column.

7 Claims, 1 Drawing Figure

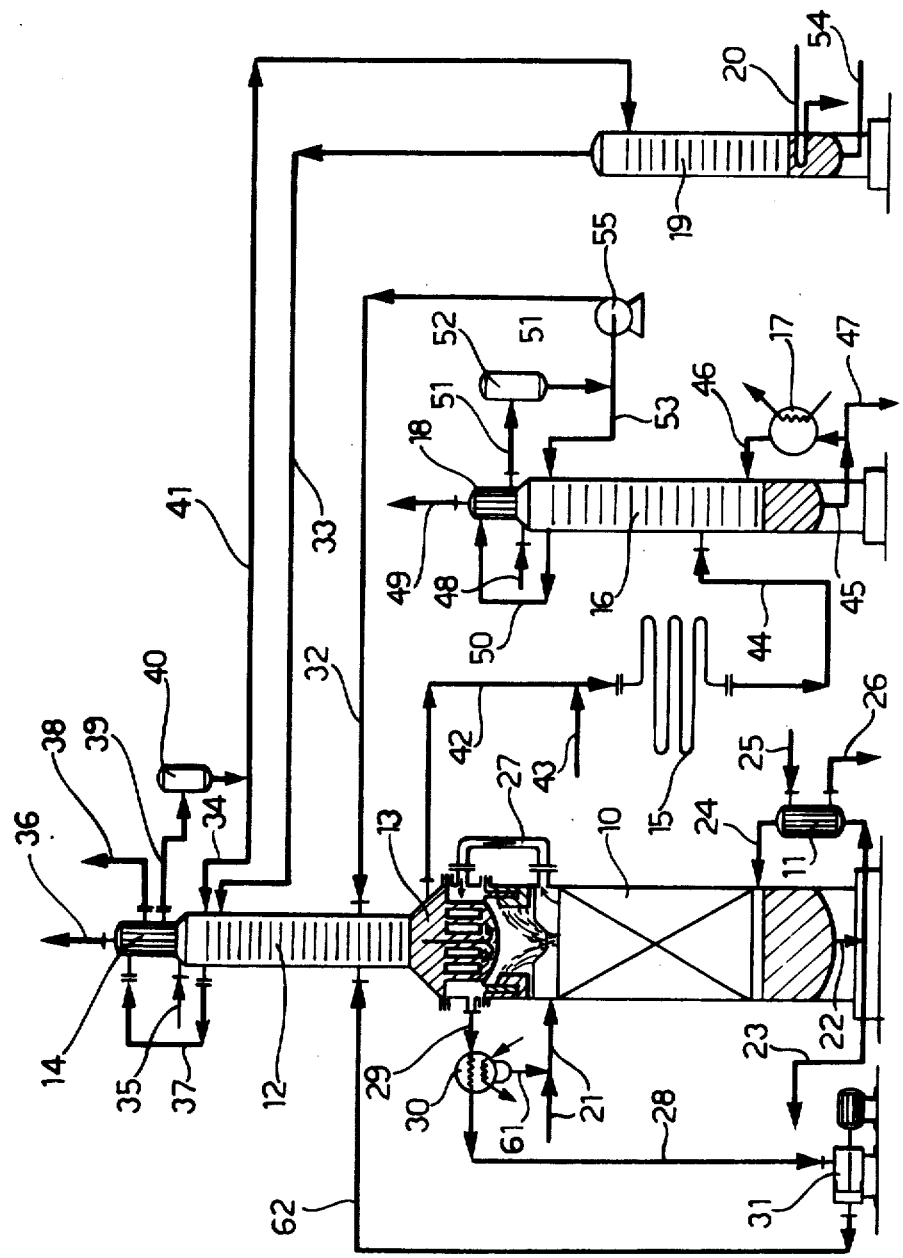

PROCESS FOR THE PURIFICATION OF ETHYLENE OXIDE

The present invention relates to the recovery of pure ethylene oxide from the solutions obtained by scrubbing with a solvent the gases deriving from the catalytic oxidation of ethylene.

Ethylene oxide is usually prepared by flowing a gaseous stream containing ethylene, oxygen and inert gases (generally nitrogen) over a silver-based catalyst at elevated temperature and at a pressure equal to or greater than atmospheric, thus obtaining a gaseous stream containing ethylene oxide, unreacted ethylene and oxygen and byproducts of the reaction (oxides of carbon and water vapour) originating from the total oxidation of ethylene, in addition to the inert gases contained in the feed and various impurities.

According to the art, this gaseous stream is scrubbed with a solvent (generally water or methanol) to yield a dilute solution of ethylene oxide from which the ethylene oxide is recovered by desorption.

The crude ethylene oxide thus obtained contains various impurities and in particular:

non-condensable substances, particularly carbon dioxide and nitrogen, absorbed together with the ethylene oxide in the scrubbing solvent;

traces of scrubbing solvent, such as water, methanol or other solvent;

the byproducts originating from the interaction of the ethylene oxide with the preselected solvent, for example glycols or glycol ethers;

acetaldehyde which is formed predominently by isomerization of the ethylene oxide.

As is known, for the production of various derivatives of ethylene oxide, for example glycols suitable for fibres, ethanolamine, detergents and other derivatives, ethylene oxide of high purity is required, in particular ethylene oxide free, or practically free, from acetaldehyde.

Indeed acetaldehyde polymerizes easily and undergoes oxidation phenomena with production of undesirable compounds, particularly colored compounds.

It is therefore necessary to purify the crude ethylene oxide.

Thus according to a known process, the crude ethylene oxide is liquefied by compression and it is then subjected to two distinct treatments, and more particularly to stripping to remove the non-condensable substances and to rectification to separate the substances having a higher boiling point than ethylene oxide. This procedure does not permit a satisfactory removal of the acetaldehyde contained in the crude ethylene oxide.

In fact whilst it is possible to remove the non-condensable substances easily (by means of the usual stripping operations) and the residual traces of scrubbing solvent (by rectification), the removal of the acetaldehyde by rectification presents considerable difficulty because of the proximity of its boiling point to that of ethylene oxide.

Therefore, according to another known technique crude ethylene oxide is fed into a fractionating column, at the top of which the greater part of the non-condensable substances is removed, while the high boiling products are removed at the bottom. Moreover, a flow of ethylene oxide with small amounts of acetaldehyde is discharged from the column at a point near the top and a flow of ethylene oxide relatively rich in acetaldehyde, at an intermediate point.

Said lateral flows are freed from the residual non-condensable substances in two separate columns.

Such a process has the disadvantages of yielding a flow of ethylene oxide whose acetaldehyde content renders it unsuitable for the majority of uses.

Also known in the art are chemical treatments, such as for example, the addition of alkaline catalysts, suitable for converting the acetaldehyde contained in the crude ethylene oxide into high boiling compounds.

In this way it becomes possible to separate by rectification the ethylene oxide from the conversion products of acetaldehyde. Such a process is not completely satisfactory because of the difficulties of obtaining an excellent purification, or better, a high conversion of the acetaldehyde (present in very low amounts in the ethylene oxide) into high boiling compounds, for example into polymeric compounds, and because of the cost of treating the whole ethylene oxide flow.

It follows that the thus purified ethylene oxide still contains non-negligible amounts of acetaldehyde as impurities.

The known processes which are based on the use of molecular sieves to separate the acetaldehyde from the crude ethylene oxide, are not completely efficient on account of the isomerism existing between the molecule of ethylene oxide and that of acetaldehyde, and are moreover burdensome and of difficult application on an industrial scale.

A simple and inexpensive process has now been found for the production of pure ethylene oxide from the crude ethylene oxide obtained by catalytic oxidation of ethylene on a silver-based catalyst.

Thus, the invention provides a process for the purification of the crude ethylene oxide present in the dilute aqueous solution resulting from the extraction with an aqueous solvent of ethylene oxide from the gaseous stream obtained by catalytic oxidation of ethylene, characterized by:

a. desorbing said crude ethylene oxide in a desorption column provided with a dephlegmator, thereby to condense in the latter water vapor issuing together with the desorbed crude ethylene oxide from the top of the desorption column;

b. liquefying by compression said desorbed crude ethylene oxide and delivering said liquefied crude ethylene oxide to a fractionating column provided with a reflux condenser, at a point intermediate the top and the bottom, said fractionating column being coupled with said desorption column thereby to use the vapor condensing in said dephlegmator as heating means for said fractionating column and being operated at a temperature of from 50° to 100° C at the bottom, at a pressure of from 4 to 15 Atmospheres and with a reflux ratio of from 0.5:1 to 6:1; discharging a gaseous stream containing non-condensable gases at the top of said reflux condenser, a liquid stream of ethylene oxide containing absorbed non-condensable gases and practically free from acetaldehyde at the bottom of said reflux condenser and a liquid stream of ethylene oxide rich in acetaldehyde at the bottom of said fractionating column;

c. treating said liquid stream discharged at the bottom of the fractionating column of (b) to convert at least 50% of the acetaldehyde present therein into high boiling products;

d. delivering said treated liquid stream of (c) to a distillation column provided with a reflux condenser, at a point intermediate the top and the bottom, operating said distillation column at a pressure of from 2 to 6 atmospheres and at a temperature of from 120° to 180° C at the bottom and discharging from said distillation column said conversion products of acetaldehyde and the substances having a higher boiling point than ethylene oxide, at the bottom, and a liquid stream containing ethylene oxide and the acetaldehyde unconverted at step (c), at the bottom of the reflux condenser, said liquid stream of (d) being recycled to the fractionating column of (b) at a point intermediate the top and the bottom; and e. removing said non-condensable gases absorbed in said liquid stream discharged at the bottom of said reflux condenser of the fractionating column of (b) in a desorption column and recovering from the latter pure ethylene oxide practically free from acetaldehyde.

The gaseous flow obtained by catalytic oxidation of ethylene on a silver-based catalyst, containing ethylene oxide, unreacted ethylene and oxygen, inert gases and various impurities, including acetaldehyde, is scrubbed with an aqueous solvent to produce an aqueous solution containing generally from 1 to 4% by weight of ethylene oxide.

The process of the present invention will now be more fully described, by way of example only, with reference to the accompanying drawing which illustrates an apparatus for carrying out an embodiment of the invention.

With reference to the drawing, the aqueous solution of ethylene oxide is fed through line 21 to desorption apparatus 10, consisting of a packed column.

The top of column 10 is maintained at a temperature of 100° C for a pressure of 1 atm, and aqueous solvent which is practically free from ethylene oxide is discharged at the bottom through pipe 22. A fraction of said aqueous solvent is recycled to column 10 through pipe 24, after passing through reboiler 11. The latter is heated with steam fed through pipe 25, the condensate being discharged through pipe 26. The remaining fraction of the solvent discharged through pipe 22 is recycled through pipe 23 to the extraction stage of ethylene oxide (not shown in the drawing).

The crude ethylene oxide issuing from the top of desorption column 10, together with aqueous vapor, is conveyed through pipe 27, to the reboiler 13 of fractionating column 12.

The aqueous vapor is thus condensed and flows back into column 10, whilst a gaseous flow of crude ethylene oxide is discharged through pipe 29. The particular coupling between desorption column 10 and fractionating column 12, illustrated in the drawing, reflects the following requirements: the operating conditions in respect of the pressure in desorption column 10 (equal or near to atmospheric), and the dangerous nature of the gaseous mixture desorbed from the aqueous solution of ethylene oxide, advise against delivering the gases issuing at the top of column 10, as heating means, to the reboiler of an adjacent column, and recycling the condensed aqueous solvent to desorption column 10.

Moreover, the thermo-degradability of ethylene oxide and the possibility of priming explosive polymerisation reactions of ethylene oxide lead to the adoption of the particular type of reboiler 13 for the fractionating column 12, in which reboiler important recirculation ratios of the liquid are obtained, owing to the thermosiphon effect.

Referring again to the drawing, the gaseous flow of ethylene oxide discharged through pipe 29 is first cooled in exchanger 30 to a temperature of the order of 20° C.

The condensed liquid separated in exchanger 30 is discharged through pipe 61, combined with the solution flowing through pipe 21 and the whole fed to column 10.

The gaseous flow of crude ethylene oxide discharged through pipe 28 typically contains an amount of acetaldehyde of the order of 200 ppm with respect to the ethylene oxide, as well as non-condensable gases (particularly nitrogen and carbon dioxide) and small amounts of water and other impurities.

The said gaseous flow is liquefied in compressor 31 at a pressure typically of the order of 6 atm and the liquid is fed through pipe 62 to fractionating column 12. The latter is a packed column, or preferably a plate column having from 10 to 70 actual plates, the liquid flow of pipe 62 being then introduced at a point between the third and the 15th plate from the bottom, according to the plate number.

The top of column 12 is fitted with a condenser 14, cooled by water fed in through pipe 35 and discharged through pipe 36.

A liquid flow of recycled ethylene oxide having an acetaldehyde content of the order of 200 ppm, is also fed into column 12 through pipe 32 at a level equal or nearly equal to that of the feed through pipe 62.

Finally, a recycled gaseous flow, formed by non-condensable gases with a variable amount of ethylene oxide, is fed into column 12 through pipe 33 at a point near the top.

The gaseous stream issuing from the top of column 12 is delivered through pipe 37 to condenser 14.

Column 12 is typically operated at a pressure of 6 atm, at a temperature of 70° C at the bottom and with a reflux ratio of the order of 3:1.

Nitrogen, carbon dioxide and other non-condensable gases present are discharged from column 12 through pipe 38. A liquid flow of ethylene oxide, practically free of acetaldehyde (less than 50 ppm) and having a content in absorbed non-condensable gases of the order of 3% by weight is discharged through pipe 39, collected in reservoir 40 and then recycled in part to column 12 as a reflux through pipe 34, the remaining fraction being sent through pipe 41 to column 19.

A liquid flow of ethylene oxide, containing the high boiling compounds and about 0.2 wt.% of acetaldehyde, is discharged through pipe 42 at the bottom of column 12.

For economical operation of the process the weight ratio between the flow of ethylene oxide discharged through pipe 41 and that discharged through pipe 42 is generally maintained at a value of the order of 8:1. The flow of ethylene oxide discharged through pipe 42 is treated in reactor 15 upon being combined with a liquid flow, fed through pipe 43, containing a substance capable of transforming the acetaldehyde into higher boiling compounds.

To this end it is possible to employ an alkaline solution which can polymerize the acetaldehyde, such as a polyoxyethylene glycol containing the corresponding alkaline glycollate in the dissolved state, or primary alcohols with a high number of carbon atoms, containing the corresponding alcholate in the dissolved state.

The acetaldehyde conversion is usually higher than 50% and conveniently less than 90%, and preferably the acetaldehyde content of the ethylene oxide discharged from reactor 15 is not less than 100 ppm.

The acetaldehyde conversion is preferably maintained at a value of the order of 80%.

The products discharged from reactor 15 are fed to distillation column 16 through pipe 44.

Column 16 is a packed column or a plate column containing from 5 to 20 actual plates, the feed being then introduced at a point between the second and 10th plate from the bottom according to the plate number. At the top of the column 16 is located a condenser 18 cooled by water fed in through pipe 48 and discharged through pipe 49. The gaseous stream escaping from the top of column 6 is delivered through pipe 50 to condenser 18.

Column 16 is typically operated under the following conditions: pressure, measured at the bottom, of 4 atm., temperature at the bottom of about 160° C and reflux ratio of the order of 1:1.

In these conditions a flow containing the conversion products of acetaldehyde, water, compounds present in the flow of pipe 43 and other possible high-boiling substances deriving, for example, from the reaction of ethylene oxide with water or the added glycols, is discharged through pipe 45 at the bottom of column 16.

Said flow is partly recycled to column 16, through line 46, upon heating in reboiler 17. The remaining fraction is discharged through pipe 47.

The flow of ethylene oxide containing the acetaldehyde not converted in reactor 15 is discharged at the top of column 16 through pipe 51, collected in reservoir 52 and then partially recycled through pipe 53 as a reflux to column 16; the remaining fraction is recycled to column 12 by means of pump 55 and pipe 32.

The flow of ethylene oxide coming from column 12 through pipe 41, is fed to column 19 where the non-condensable gases are removed, operating at a pressure of the order of 6 atm and maintaining a temperature at the bottom of about 65° C by heating with steam flowing through coil 20.

The gaseous flow escaping at the top of column 19 is recycled to column 12, at a point near its top, by means of pipe 33.

Ethylene oxide of a purity equal to or in excess of 99.995%, having an acetaldehyde content equal to or generally below 50ppm is recovered at the bottom of column 19 through pipe 54.

EXAMPLE

Referring to the drawing, an aqueous solution containing 2.5% by weight of ethylene oxide, 0.11% by weight of carbon dioxide and 0.02% by weight of nitrogen is fed to the desorption column 10 through pipe 21. An amount of 200ppm of acetaldehyde with respect to the ethylene oxide is also present in the solution.

A flow consisting of practically pure water, is extracted from the bottom of column 10, through pipe 23, whilst through pipe 29 at the top of the condenser-reboiler 13, at a pressure of 1.13 Kg/cm$^2$ abs. and at a temperature of 78° C, a gaseous mixture is extracted with the following volumetric composition: 40% water vapor, 2.5% carbon dioxide, 0.7% nitrogen, the remaining percentage consisting of ethylene oxide and impurities.

This gaseous flow passes to the final condenser 30, where the greater part of the water vapor condenses.

The condensate is discharged through pipe 61 and combined with the flow of pipe 21, and the whole is finally delivered to column 10. The gaseous mixture is issued through pipe 28 at a pressure of 1.1 Kg/cm$^2$ abs. and at a temperature of 15° C.

Said gaseous mixture contains 1.6% by volume of water vapor, 4.2% by volume of carbon dioxide, 1.2% by volume of nitrogen, the remaining percentage consisting of ethylene oxide and impurities.

This mixture is compressed in compressor 31 to 5.6 Kg/cm$^2$ abs. and delivered to column 12, at a level corresponding to the 10th plate from the bottom, column 12 being fitted with valve plates.

Column 12 contains 40 actual plates and a reflux ratio of 3:1 is maintained between the flow recycled through pipe 34 and that discharged through pipe 41. At the bottom of column 12 the pressure is 5.7 Kg/cm$^2$ abs. and the temperature is 65° C. From the bottom of said column, at the level of the reboiler, a flow of ethylene oxide equal to 15% by weight of the ethylene oxide fed through pipe 62 is extracted through pipe 42. This flow contains nearly the whole of the water present in the feed of pipe 62 and a large part of the acetaldehyde impurity; more precisely this flow contains 4.4% by weight of water, 0.11% by weight of acetaldehyde, the remaining percentage consisting of ethylene oxide.

A flow containing ethylene oxide and non-condensable gases is extracted from the top of the column at the level of the first plate and is passed through pipe 37 to the top of condenser 14. This condenser is cooled by water circulation in exchange tubes, the water being introduced at 25° C through pipe 35 and extracted through pipe 36.

A gaseous flow consisting of all the non-condensable gases contained in the feed flow 28, as well as a percentage of ethylene oxide depending on the vapor pressure of the latter at the operating temperature, is discharged from the condenser through line 38, at a pressure of 5.4 Kg/cm$^2$ abs. and at 30° C.

More precisely this gaseous flow comprises 47.5% by volume of carbon dioxide and 13.5% by volume of nitrogen, the remainder being ethylene oxide. This flow is passed to a water absorption column for the recovery of the ethylene oxide.

A liquid flow consisting for the most part of ethylene oxide, with small amounts of absorbed carbon dioxide and nitrogen and containing negligible amounts of acetaldehyde, is extracted at 30° C from the bottom of condenser 14, through pipe 39. This liquid flow is collected in reservoir 40, from whence the two flows 34 and 41 are extracted. The flow 34 is delivered to column 12 at the level of last plate from the bottom, whilst the flow 41 is delivered to the top of plate column 19.

This flow 41 consists for the most part of ethylene oxide in a quantity equal to 1:1 times that of the ethylene oxide fed through pipe 62.

The liquid flow 41 contains 2.2% by weight of carbon dioxide, 50 ppm of nitrogen and 43 ppm of acetaldehyde.

The desorption of the non-condensable gases (principally carbon dioxide) contained in flow 41, is carried out in sieve plate column 19 by heating with the steam circulating in coil 20 at the bottom of the column.

Column 19 has 12 actual plates and a gaseous flow comprising all the carbon dioxide and nitrogen contained in the feed and a quantity of ethylene oxide equal to 0.16 times the quantity of ethylene oxide contained in the feed to column 10 through pipe 62, is discharged at the top which is maintained at 5.6 Kg/cm² abs.

From the bottom of column 19, maintained at 5.7 Kg/cm² abs. and at 63° C, a flow of purified ethylene oxide is extracted through pipe 54.

The weight ratio of this flow to the ethylene oxide present in the feed to column 12 through pipe 62, is equal to 94:100.

The flow 54 consists of practically pure ethylene oxide, in that the acetaldehyde content is 50 ppm.

A liquid flow of polyoxyethylene glycol of molecular weight 300, containing 4% by weight of potassium in the form of the corresponding potassium glycollate, is added through pipe 43 to he flow extracted at 65° C at the bottom of column 12 through pipe 42. The weight ratio of flow 43 to flow 42 is equal to 3:100.

The mixture thus obtained is passed to adiabatic reactor 15, of the "plug-flow" type, consisting of a coil ensuring a reaction time of 10 minutes.

The polymerisation of a fraction of the acetaldehyde occurs in reactor 15. In particular the liquid effluent discharged through pipe 44 from reactor 15 contains 200 ppm of acetaldehyde with respect to ethylene oxide, the remaining part of the acetaldehyde having been converted to high-boiling polymer.

This effluent is fed to the fifth plate from the bottom of sieve plate column 16 having 15 actual plates.

All the water contained in said effluent, the acetaldehyde polymer produced in reactor 15, as well as the constituents of flow 43, that is the alkaline glycollates in polyoxyethylene glycol, are extracted from the bottom of the column through line 47.

The pressure at the bottom of column 16 is 4 Kg/cm² abs. and the temperature 160° C.

The gaseous flow issued from the top of column 16 at the level of the first plate through pipe 50, is delivered to condenser 18 cooled by water circulation.

A flow of condensate is extracted from the bottom of condenser 18, and collected in the small reflux tank 52, maintained at a pressure of 3.8 Kg/cm² abs. and at 30° C.

Two flows having a 1:1 weight ratio are extracted from this tank. The first one is returned as reflux, through pipe 53, to column 16 at the level of the last plate from the bottom, whilst the second is recycled, through pump 55 and pipe 32, to column 12 at the level of the 10th plate from the bottom. This last flow (pipe 32) consists of the whole of the ethylene oxide discharged from column 12 through pipe 42, and of 200 ppm of acetaldehyde with respect to the ethylene oxide.

We claim:

1. A method for the purification of the crude ethylene oxide present in the dilute aqueous solution resulting from the extraction with an aqueous solvent of ethylene oxide from the gaseous stream obtained by catalytic oxidation of ethylene, which comprises the steps of:
   a. desorbing said crude ethylene oxide in a desorption column provided with a dephlegmator, thereby to condense in the latter water vapor issuing together with the desorbed crude ethylene oxide from the top of the desorption column;
   b. liquefying by compression said desorbed crude ethylene oxide and delivering said liquefied crude ethylene oxide to a fractionating column provided with a reflux condenser, at a point intermediate the top and the bottom, said fractionating column being coupled with said desorption column thereby to use the vapor condensing in said dephlegmator as heating means for said fractionating column and being operated at a temperature of from 50° to 100° C at the bottom, at a pressure of from 4 to 15 Atmospheres and with a reflux ratio of from 0.5:1 to 6:1, discharging a gaseous stream containing non-condensable gases at the top of said reflux condenser, a liquid stream of ethylene oxide containing absorbed non-condensable gases and practically free from acetaldehyde at the bottom of said reflux condenser and a liquid stream of ethylene oxide rich in acetaldehyde at the bottom of said fractionating column;
   c. treating said liquid stream discharged at the bottom of the fractionating column of (b) to convert at least 50% of the acetaldehyde present therein into high boiling products;
   d. delivering said treated liquid stream of (c) to a distillation column provided with a reflux condenser, at a point intermediate the top and the bottom, operating said distillation column at a pressure of from 2 to 6 atmospheres and at a temperature of from 120° to 180° C at the bottom and discharging from said distillation column said conversion products of acetaldehyde and the substances having a higher boiling point than ethylene oxide, at the bottom, and a liquid stream containing ethylene oxide and the acetaldehyde unconverted at step (c), at the bottom of the reflux condenser, said liquid stream of (d) being recycled to the fractionating column of (b) at a point intermediate the top and the bottom; and
   e. removing said non-condensable gases absorbed in said liquid stream discharged at the bottom of said reflux condenser of the fractionating column of (b) in a desorption column and recovering from the latter pure ethylene oxide practically free from acetaldehyde.

2. The method of claim 1, wherein said fractionating column of (b) is a column having from 10 to 70 plates, said crude ethylene oxide being introduced at a point between the third and the 15th plate from the bottom according to the plate number of said column of (b).

3. The method of claim 1, wherein said fractionating column of (b) is operated at a pressure of 6 atm, at a temperature of 70° C at the bottom and with a reflux ratio of 3:1, while maintaining a 8:1 weight ratio between said liquid stream discharged at the bottom of said reflux condenser of (b) and said liquid stream discharged at the bottom of said column (b).

4. The method of claim 1, wherein from 50 to 90% of the acetaldehyde present in said liquid stream treated in (c), is converted into high-boiling products.

5. The method of claim 1, wherein said distillation column of (d) is a column having from five to 20 plates, said liquid stream treated in (c) being introduced at a point between the second and the 10th plate from the bottom, according to the plate number of said column of (d).

6. The method of claim 1, wherein said column of (d) is operated at a pressure of 4 atm at the bottom, at a temperature of 160° C at the bottom and with a reflux ratio of 1:1.

7. The method of claim 1, wherein said column of (e) is operated at a pressure of 6 atm and at a temperature of about 65° C at the bottom.

* * * * *